United States Patent [19]

Takita et al.

[11] Patent Number: 5,140,020

[45] Date of Patent: * Aug. 18, 1992

[54] DERIVATIVE OF DIHYDROXYBENZAMIDE AND A PHARMACEUTICAL COMPOSITION THEREOF

[75] Inventors: Hitoshi Takita; Sakuo Noda, both of Tokyo; Yutaka Mukaida, Saitama; Kazuyoshi Inada, Tokyo; Mari Toji, Tokyo; Fumihiko Kimura, Tokyo; Toyohiko Nitta, Tokyo; Kohju Watanabe, Sakado; Kiyonori Umekawa, Urayasu; Hidetoshi Kobayashi, Tokyo, all of Japan

[73] Assignee: Kureha Kagatu Kogyo Kabushiki Kaisha, Tokyo, Japan

[ * ] Notice: The portion of the term of this patent subsequent to Feb. 16, 2005 has been disclaimed.

[21] Appl. No.: 719,118

[22] Filed: Jun. 20, 1991

Related U.S. Application Data

[60] Division of Ser. No. 432,350, Nov. 6, 1989, abandoned, which is a continuation of Ser. No. 116,975, Nov. 5, 1987, abandoned, which is a continuation of Ser. No. 939,241, Dec. 8, 1986, Pat. No. 4,725,598, which is a continuation of Ser. No. 649,720, Sep. 12, 1984, abandoned.

[30] Foreign Application Priority Data

Sep. 13, 1983 [JP] Japan .................. 58-168936

[51] Int. Cl.$^5$ ........................... A61K 31/165
[52] U.S. Cl. ....................... 514/166; 514/622
[58] Field of Search ............... 564/177, 179; 514/166, 514/622

[56] References Cited

U.S. PATENT DOCUMENTS

| | | | |
|---|---|---|---|
| 2,848,335 | 8/1958 | Bell et al. | 526/544 |
| 2,849,480 | 8/1958 | Kreuchunas | 564/177 |
| 3,148,997 | 9/1964 | Hemwall | 564/177 X |
| 4,263,322 | 4/1981 | van't Riet et al. | 564/177 |
| 4,302,448 | 11/1981 | Bickel et al. | 514/12 |
| 4,394,389 | 9/1983 | van't Riet et al. | 564/177 |
| 4,448,730 | 5/1984 | van't Riet et al. | 564/170 |
| 4,725,598 | 2/1988 | Tahita et al. | 564/177 X |

FOREIGN PATENT DOCUMENTS

| | | | |
|---|---|---|---|
| 0059108 | 1/1982 | European Pat. Off. | |
| 142241 | 5/1985 | European Pat. Off. | 514/622 |
| 1141986 | 1/1963 | Fed. Rep. of Germany. | |
| 2077790 | 11/1971 | France | 514/166 |
| 391702 | 5/1965 | Hungary. | |
| 29467 | 3/1976 | Japan. | |
| 163812 | 8/1985 | Japan | 514/622 |
| 199850 | 10/1985 | Japan | 514/622 |

OTHER PUBLICATIONS

Dorland, *Medical Dictionary*, p. 1151.
CA 85-177027v (1976).
CA 85-94115n (1976).
CA 81-120190f (1974).
CA 74-112752f (1971).
CA 76-21107z (1972).
CA 85-142860j.

*Primary Examiner*—Carolyn Elmore
*Attorney, Agent, or Firm*—Cushman, Darby & Cushman

[57] ABSTRACT

Disclosed herein are a derivative of dihydroxybenzamide represented by the formula(I):

$$(OH)_2\text{-}C_6H_3\text{-}\underset{\underset{O}{\|}}{C}\text{-}N\begin{array}{c}R^1\\R^2\end{array}$$

wherein (1) $R^1$ represents a hydrogen atom or a lower alkyl group and $R^2$ represents a straight chain-alkyl group of 4 to 12 carbon atoms, a branched chain-alkyl group of 4 to 12 carbon atoms, a cyclo-alkyl group of 4 to 12 carbon atoms, $$\text{-}(CH_2)_n\text{-}C_6H_5$$

wherein n is an integer of 1 to 6, or a pyridyl group which is substituted or unsubstituted, or (2) $R^1$ and $R^2$ are cyclized to make a heterocycle containing amino group represented by the formula
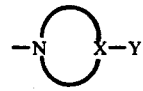
wherein X represents a nitrogen atom or a methine and Y represents a hydrogen atom, an alkyl group of 1 to 6 carbon atoms or a phenyl group, and a pharmaceutical composition containing the same.
4 Claims, 3 Drawing Sheets

DERIVATIVE OF DIHYDROXYBENZAMIDE AND A PHARMACEUTICAL COMPOSITION THEREOF

This is a division of application Ser. No. 07/432,350, filed Nov. 6, 1989, now abandoned which is a continuation of Ser. No. 07/116,975 filed Nov. 5, 1987 now abandoned, which is a continuation of Ser. No. 06/939,241 filed Dec. 8, 1986 now issued U.S. Pat. No. 4,725,598, which is a continuation of Ser. No. 06/649,720 filed Sep. 12, 1984, now abandoned.

DETAILED DESCRIPTION OF THE INVENTION

Figure 1:
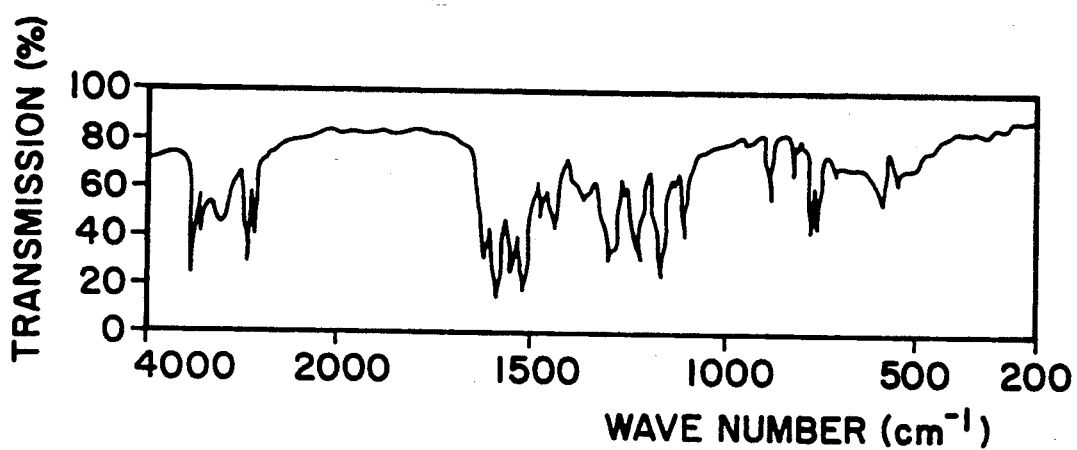
Figure 2:
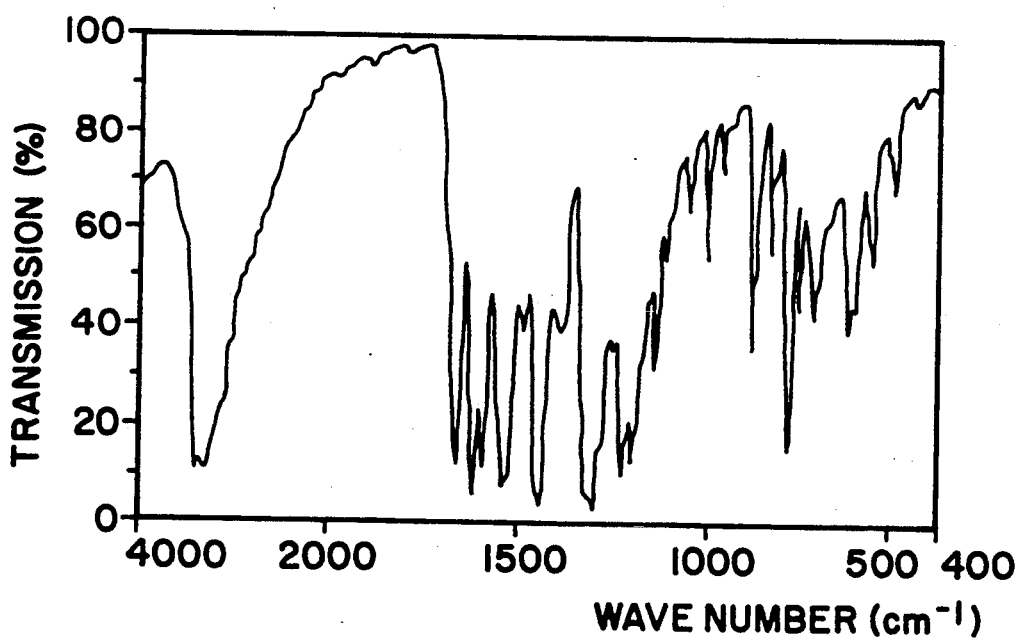
Figure 3:
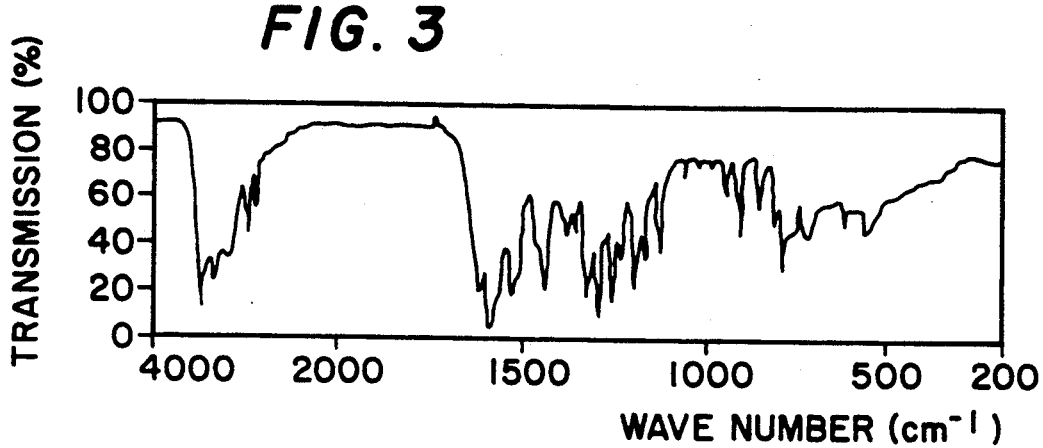
Figure 4:
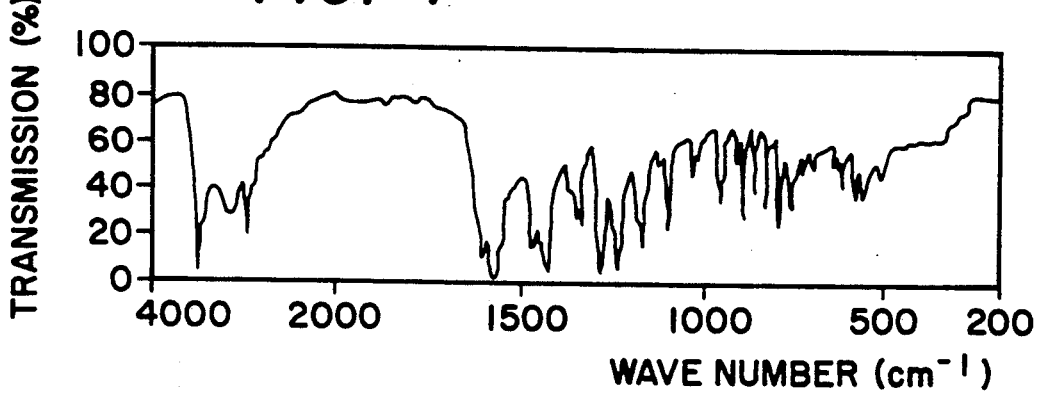
Figure 5:
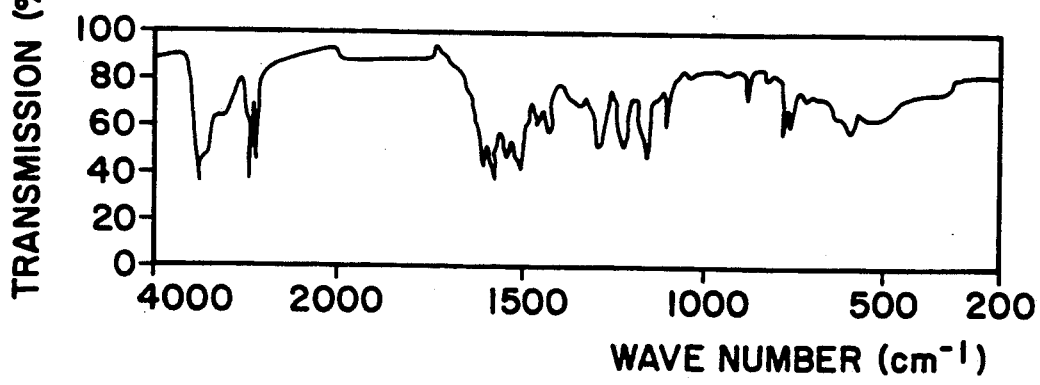
Figure 6:
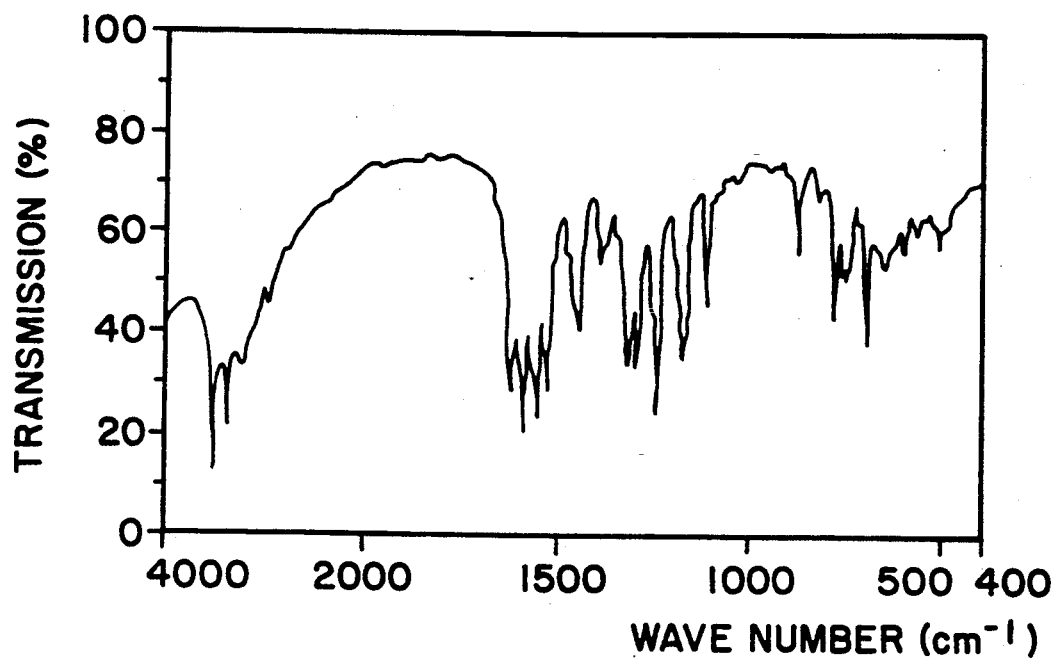
Figure 7:
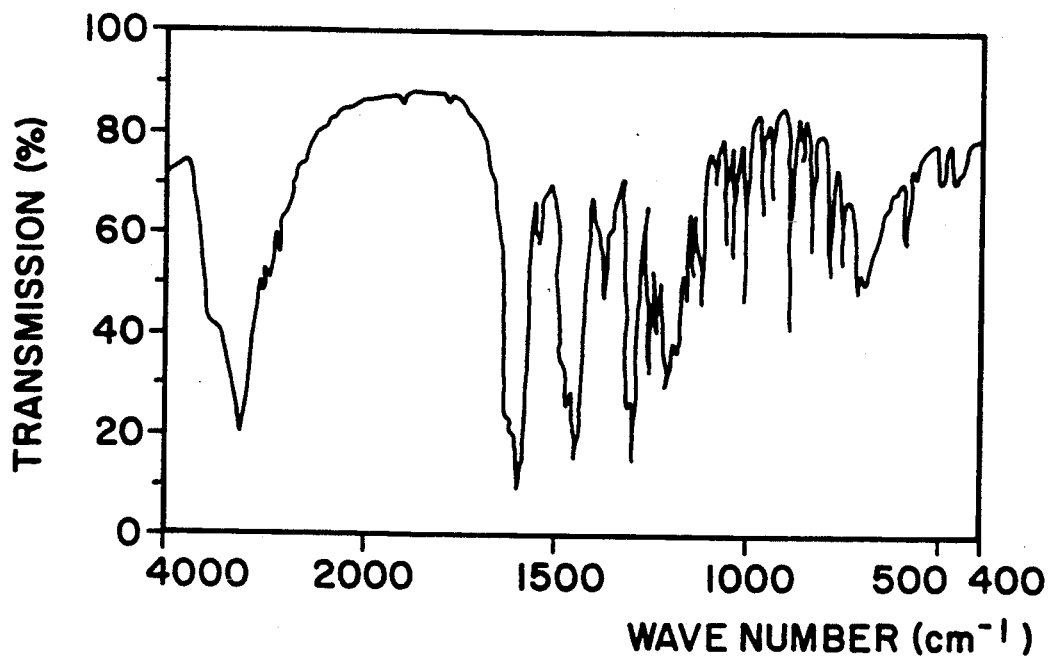

The present invention relates to a derivative of dihydroxybenzamide represented by the formula (I):

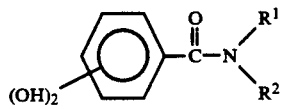

wherein (1) $R^1$ represents a hydrogen atom or a lower alkyl group and $R^2$ represents a straight chain-alkyl group of 4 to 12 carbon atoms, a branched chain-alkyl group of 4 to 12 carbon atoms, a cyclo-alkyl group of 4 to 12 carbon atoms,

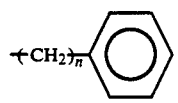

wherein n is an integer of 1 to 6, or a pyridyl group which is substituted or unsubstituted, or (2) $R^1$ and $R^2$ are cyclized to make a heterocycle containing an amino group represented by the formula

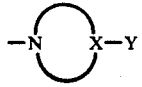

wherein X represents a nitrogen atom or a methine and Y represents a hydrogen atom, an alkyl group of 1 to 6 carbon atoms or a phenyl group, and pharmaceutical composition containing the same, and more in detail, the present invention relates to a derivative of (a) N-(alkyl)-dihydroxybenzamide represented by the formula (I) wherein $R^1$ is a hydrogen atom and $R^2$ is a straight chain-alkyl group of 4 to 12 carbon atoms, a branched chain-alkyl group of 4 to 12 carbon atoms or a cyclo-alkyl group of 4 to 12 carbon atoms, (b) N-(ω-phenylalkyl)-dihydroxybenzamide represented by the formula (I) wherein $R^1$ is a hydrogen atom and $R^2$ is

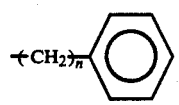

wherein n is an integer of 1 to 6, (c) N-(pyridyl)-dihydroxybenzamide represented by the formula (I) wherein $R^1$ is a hydrogen atom and $R^2$ is a pyridyl group which is substituted or unsubstituted and (d) dihydroxybenz-piperidide or dihydroxybenzpiperazide derivatives having a group represented by the formula,

wherein $R^1$ and $R^2$ are cyclized to make a corresponding heterocyclic structure.

In the aspect of the present invention, there is provided derivative of dihydroxybenzamide represented by the formula (I):

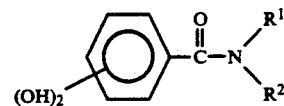

wherein (1) $R^1$ represents a hydrogen atom or a lower alkyl group and $R^2$ represents a straight chain-alkyl group of 4 to 12 carbon atoms, a branched chain-alkyl group of 4 to 12 carbon atoms, a cyclo-alkyl group of 4 to 12 carbon atoms,

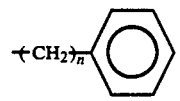

wherein n is an integer of 1 to 6, or a pyridyl group which is substituted or unsubstituted, or (2) $R^1$ and $R^2$ are cyclized to make a heterocycle containing an amino group represented by the formula

wherein X represents a nitrogen atom or a methine group and Y represents a hydrogen atom, an alkyl group of 1 to 6 carbon atoms or a phenyl group.

In a second aspect of the present invention, there is provided a pharmaceutical composition in dosage unit form, which comprises a dosage amount of a derivative of dihydroxybenzamide represented by the formula (I):

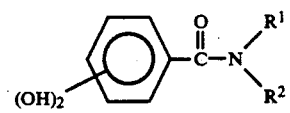

wherein (1) $R^1$ represents a hydrogen atom or a lower alkyl group and $R^2$ represents a straight chain-alkyl group of 4 to 12 carbon atoms, a branched chain-alkyl group of 4 to 12 carbon atoms, a cyclo-alkyl group of 4 to 12 carbon atoms,

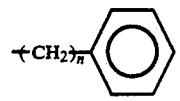

wherein n is an integer of 1 to 6, or a pyridyl group which is substituted or unsubstituted, or (2) $R^1$ and $R^2$ are cyclized to make a heterocycle containing an amino group represented by the formula

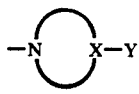

wherein X represents a nitrogen atom or a methine group and Y represents a hydrogen atom, an alkyl group of 1 to 6 carbon atoms or a phenyl group.

In a third aspect of the present invention, there is provided a method for the treatment of inflammatory diseases, which comprises administering to patients suffering from inflammatory diseases an effective amount of a derivative of dihydroxybenzamide represented by the formula (I):

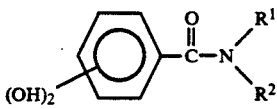

wherein (1) $R^1$ represents a hydrogen atom or a lower alkyl group and $R^2$ represents a straight chain-alkyl group of 4 to 12 carbon atoms, a branched chain-alkyl group of 4 to 12 carbon atoms, a cyclo-alkyl group of 4 to 12 carbon atoms,

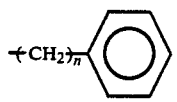

wherein n is an integer of 1 to 6, or a pyridyl group which is substituted or unsubstituted, or (2) $R^1$ and $R^2$ are cyclized to make a heterocycle containing amino group represented by the formula

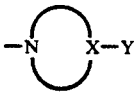

wherein X represents a nitrogen atom or a methine group and Y represents a hydrogen atom, an alkyl group of 1 to 6 carbon atoms or a phenyl group.

Of the attached drawings, FIGS. 1 to 7 are infrared absorption spectra of the respective present compounds, Compound Nos. 1 to 7.

The compound according to the present invention is synthesized following the known methods, and the compound according to the present invention can be profitably synthesized by the following method while using dihydroxybenzoic acid and one of various amines as the starting material.

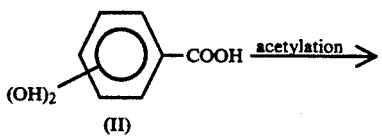

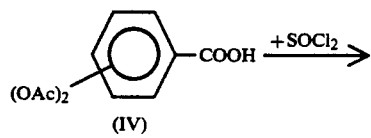

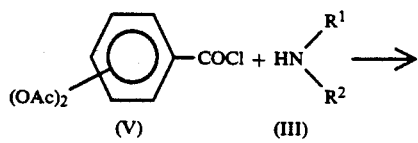

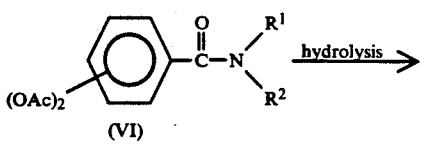

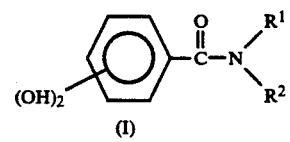

As a dihydroxybenzoic acid used herein as one of the starting materials, represented by the formula (II), one of various dihydroxybenzoic acids is used and particularly 2,5-dihydroxybenzoic acid or 3,4-dihydroxybenzoic acid is excellent in a pharmacological view point.

As an amine represented by the formula (III), a primary amine wherein $R^1$ is a hydrogen atom or a secondary amine wherein $R^1$ is a lower alkyl group of 1 to 4 carbon atoms may be used. As the primary amide, alkylamines with a straight carbon chain or a branched carbon chain such as propylamine, butylamine, octylamine, dodecylamine and the like, ω-phenylalkylamines such as ω-phenylethylamine, ω-phenylpropylamine and the like, cyclohexylamines, aminopyridines such as 3-aminopyridine and 4-aminopyridine and those aminopyridines having substituent(s) on the pyridine ring may be exemplified. As the secondary amines, N-methyl-octylamine, N-methyl-cyclohexylamine, piperidine and N-substituted piperazine such as N-methylpiperazine and N-phenylpiperazine may be exemplified.

In the case when an organic acid anhydride such as acetic anhydride is reacted with a dihydroxybenzoic acid represented by the formula (II) in the presence of an alkali such as potassium hydroxide or an acid catalyst such as sulfuric acid and the like, a diacetoxybenzoic acid represented by the formula (IV) is obtained, the reaction being carried out at a temperature of from room temperature to 50° C. for 2 min to one hour. By reacting the thus obtained compound (IV) with a chlorinating agent such as thionyl chloride, phosphorus trichloride, oxalyl chloride and the like under a reflux condenser for 10 min to 3 hours, preferably for 20 to 40 min while stirring, diacetoxybenzoyl chloride (V) is obtained.

In addition, the reaction for a long time period should not be carried out, otherwise, the yield of the objective compound is reduced by the occurrence of side reactions.

The diacetyl derivative (VI) of the objective compound is obtained by reacting the compound (V) with a primary amine or a secondary amine represented by the formula (III) in an organic solvent and in the presence of a hydrogen chloride-capture agent at a temperature of lower than 35° C. for 30 min to 2 hours. As the hydrogen chloride-capture agent, tertiary amine such as triethylamine which does not participate in the reaction previously mentioned. As the organic solvent, any organic solvent may be used without any limitation provided that it is a non-polar solvent which does not participate in the reaction. Usually dichloromethane and chloroform are preferably used.

The hydrolysis of the compound (VI) to the object compound (I) is carried out in an aqueous methanolic solvent at a temperature of lower than 50° C., preferably at a temperature of from 5° to 30° C. In the case where the reaction temperature is higher than 50° C., the reaction is apt to be accompanied by side reactions. After the reaction is over, the reaction mixture is treated by a known method to obtain the compound (I) as the objective compound of the present invention.

In addition, the above-mentioned process is an exemplary method for obtaining the compound of the present invention (hereinafter referred to as the present compound) and accordingly, the process for producing the present compound is not to be limited to the above-mentioned process.

The present compound (I) shows an anti-inflammatory activity and particularly, shows an excellent effect in treatment against chronic inflammatory diseases. Namely, a derivative of dihydroxybenzamide according to the present invention shows an activity of inhibiting platelet aggregation, reducing leucotaxis, inhibiting granuloma formation, inhibiting adjuvant arthritis and inhibiting the process of lesion on the animals, suffering from an autoimmune disease NZB/WF$_1$, MRL/1 mouse, and an activity of inhibiting the production of SRS-A in the sensitized lungs of guinea pig.

In addition, the acute toxicity is extremely low (LD$_{50}$ of larger than 2000 mg/kg body weight).

Accordingly, the present compound is useful as a medicine for preventing and/or treating rheumatism, the collagen diseases such as SLE, etc., the chronic diseases such as nephritis (nephritic syndrome), etc. and asthma. In addition, the diacetyl derivatives of the present invention are converted into the dihydroxy derivatives (I) within living body and accordingly, the derivatives of diacetylbenzamide represented by the formula (VI) is also useful as such a medicine.

The present compound can be administered orally, rectally or injected as a pharmaceutical composition comprising a dosage amount of the present compound and pharmaceutically acceptable carrier(s) and/or adjuvant(s) in several forms of the composition. In such a case, more than two forms of the present compounds can be used together, and another pharmaceutically active substance(s) may be combined with the present compound.

As the form of the pharmaceutical composition comprising the present compound, tablet, sublingual tablet, powder, capsule, troche, aqueous solution, oily solution, suspension, emulsion, syrup, aqueous solution for injection, oily solution for injection and others may be exemplified.

As a pharmaceutically acceptable carrier for the present compound in the pharmaceutical composition, water, gelatin, lactose, starch, pectin, stearic acid, magnesium stearate, talc, vegetable oils, gum arabic, polyalkylene glycol, vaseline, sorbitan trioleate, polyoxyethylene sorbitan monooleate, alkylphenol, aliphatic alcohols and polyvinylpyrrolidone may be exemplified.

Further, in the preparation of the pharmaceutical composition according to the present invention, it is possible, if necessary, to use a sweetening agent, seasonings, a coloring agent, a preservative, a salt for adjusting osmotic pressure, a buffering agent, etc. which are generally used as a pharmaceutical adjuvant. The content of the present compound in the pharmaceutical composition may be selected within the range of from 0.01 to 100% by weight, preferably from 0.05 to 80% by weight.

Although the pharmaceutical composition comprising the present compound may be administered orally or parenterally to human and mammals, oral administration including sublingual administration is preferable. The parenteral administration includes injection administration (for instance, subcutaneous, intramuscular and intravenous injection and dropping) and rectal administration.

The dose rate of the present invention compound is, in the general human cases, 0.1 to 500 mg/kg body weight/day, preferably, 0.5 to 200 mg/kg/day, more preferably, 2 to 60 mg/kg/day in oral administration, and 0.01 to 200 mg/kg/day, preferably, 0.1 to 100 mg/kg/day, more preferably, 0.5 to 20 mg/kg/day in parenteral administration, and the daily amount is divided into one to four portions to be administered once to four times in one day. However, since the dosage depends on the species, the age, the individual difference and the disease state of the object to be administered, there are cases where an amount of the present compound over or below the above-mentioned range is administered.

The toxicological and pharmacological properties of the present compounds are shown on the representative member thereof as follows.

(1) Acute toxicity

The acute toxicity (LD$_{50}$) of each of the following seven present compounds (Nos. 1 to 7) was over 2000 mg/kg as the result of observation during 7 days after administration on the groups of female Jcl-ICR mice of 4 weeks after birth to each of which an aqueous suspension of each of the seven present compounds in an aqueous 0.3% solution of carboxymethylcellulose was orally administered.

The present substances used in the acute toxicity test were as follows.

No. 1 N-(n-octyl)-3,4-dihydroxybenzamide

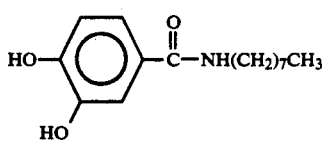

No. 2 N-(2-pyridyl)-3,4-dihydroxybenzamide

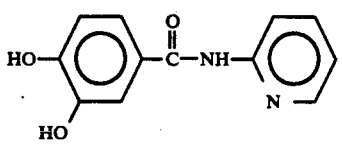

No. 3 N-(n-butyl)-3,4-dihydroxybenzamide

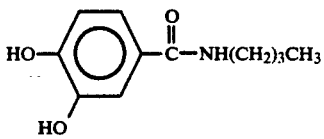

No. 4 3,4-dihydroxybenzpiperidide

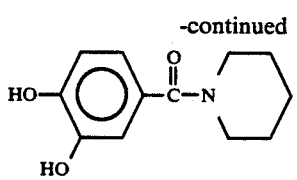

No. 5 N-(n-dodecyl)-3,4-dihydroxybenzamide

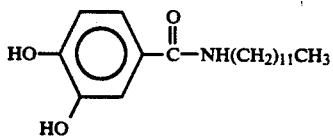

No. 6 N-(ω-phenylpropyl)-3,4-dihydroxybenzamide

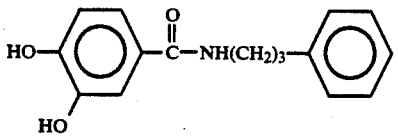

No. 7 3,4-dihydroxybenz-N-methylpiperazide

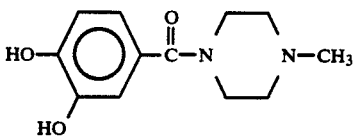

(2) Inhibitory activity of platelet aggregation

After collecting blood specimen from the auricular vein of a male rabbit of an ordinary race in the presence of citrate, the thus collected blood was subjected to centrifugation to obtain a platelet-rich plasma (PRP) and a platelet-poor plasma (PPP) therefrom. The plasma containing 300,000 platelets/μl was prepared by diluting the PRP with the PPP, and divided equally into two portions.

Into the first portion of the thus obtained plasma mixture, as control, dimethylsulfoxide was added, and then, an aqueous solution of sodium arachidonate as an aggregation agent prepared by dissolving thereof into a saline solution was added to the resultant mixture to adjust the final concentration of the arachidonate wherein to 400 μM.

On the other hand, into the second portion thereof, a solution of each of the present compounds shown in Table 1 in dimethylsulfoxide was added, and then, the above-mentioned aqueous solution of sodium arachidonate was added to the resultant mixture.

The platelet aggregation reactions were measured with the aid of a platelet aggregation tracer (model PAT-4A, made by NIKO Bioscience Co., Ltd.) and its $IC_{100}$ values (the concentration of an agent necessary for inhibiting platelet aggregation perfectly) are shown in Table 1.

TABLE 1

| Present compound | $IC_{100}$ (μM) |
| --- | --- |
| No. 1 | <18 |
| No. 2 | 25 |
| No. 3 | 45 |
| No. 4 | 65 |
| No. 5 | <18 |
| No. 6 | 80 |
| No. 7 | 300 |

In Table 1, all of the present compounds tested inhibited the platelet aggregation using sodium arachidonate.

(3) Inhibitory activity of the migration of polymorphonuclear leukocytes

The activity of each of the present compounds in in vivo inhibition of the migration of polymorphonuclear leukocytes was examined by the pouch-CMC method presented by Ishikawa (refer to J. Pharmaceut. Soc., Japan, 88, 1472, 1968) using male Donryu rats.

After cutting the hairs on the back of each male Donryu rat at a 5 cm square, 5 ml of air were subcutaneously injected into the hair-cut position, and after 24 hours of the injection, 5 ml of a 0.2% solution of sodium carboxymethylcellulose in a saline was injected into the pouch made by the injected air.

After dividing the rats into 3 groups, an aqueous 0.2% solution of carboxymethylcellulose was orally administered to each rat of the first group at a rate of 1 ml/100 g body weight (as control), and each of the present compounds (Compounds Nos. 1, 2 and 4) was orally administered to each rat of the second group after suspending the compound in an aqueous 0.2% solution of carboxymethylcellulose. Each rat of the third group is orally administered with an aqueous solution of indomethacin as positive control.

After 3 and 6 hours of the injection, the exudates in the pouch were collected from each rat, and the number of polymorphonuclear leukocytes (hereinafter referred to as PMN) exudated was counted and, the results are shown in Table 2.

TABLE 2

| Group | Amount of administration (mg/kg) | Number of PMN in exudated liquid (number/mm³) × 10³ | | Inhibition rate of exudation of PMN (%) | |
| --- | --- | --- | --- | --- | --- |
| | | after 3 hr | after 6 hr | after 3 hr | after 6 hr |
| Control | — | 4.9 | 21.8 | — | — |
| Test groups | | | | | |
| Compound No. 1 | 50 | 2.4 | 16.8 | 51.0 | 22.9 |
| No. 2 | 50 | 2.3 | 13.6 | 53.1 | 37.6 |
| No. 4 | 50 | 2.6 | 16.3 | 46.9 | 25.2 |
| Positive[1] control | 3 | 3.9 | 17.0 | 20.4 | 22.0 |

Note:
[1] Administered with indomethacin

As in Table 2, the present compound inhibited the migration of the polymorphonuclear leukocyte into the pouch, namely the inflammatory lesion.

(4) Inhibitory activity of the granuloma formation

The activity of the present invention compounds in inhibiting the granuloma formation was examined according to the method of Fujimura et al. (refer to "OYO YAKURI, 19(3), 329(1981)) while using 5 week old male Donryu rats after birth as follows.

After burying a paper disk of 13 mm in diameter and 0.26 mm in thickness immersed in an aqueous 2% solution of carboxymethylcellulose (hereinafter referred to as CMC) containing both dihydroxystreptomycia and penicillin (both of $10^6$ unit at a rate of 0.1 mg/ml) into the back of each rat under anesthesia by ether, the rats were divided into four groups. To rats of the first group, an aqueous 0.3% solution of CMC was orally administered every day for 10 days, to rats of the second group, an aqueous dispersion of one of the present compounds shown in Table 3 in an aqueous 0.3% solution of CMC was orally administered every day for 10 days and to rats of the third and fourth groups, an aqueous 0.3% solution of CMC containing either indomethacin or prednisolone was orally administered every day for 10 days.

The granuloma formed was extirpated on the eleventh day after the implantation and weighed, as the results are shown in Table 3.

method of Fujihira et al. (refer to "OYO YAKURI", 5(2), 169, (1971)) as follows.

Groups of 8 rats were used, and to each rat of a group while under anesthesia by ether, a Freund's complete adjuvant dissolved in mineral oil at a concentration of 0.6 mg/0.1 ml was injected intradermally into the trail thereof.

After 3 weeks of the injection, to each rat of a group an aqueous dispersion of one of the present compounds shown in Table 4 in an aqueous 0.3% solution of CMC was orally administered every day for 14 days, and to each of the control group, the aqueous 0.3% solution of CMC was administered in a similar manner, with each rat of the positive control group being treated with the similar oral administration of prednisolone in the aqueous 0.3% solution of CMC. The volume of the hind paw of each rat was measured on the day of starting the

TABLE 3

| Group | Amount of administration (mg/kg/day) | Weight of dried granuloma (mg) | Rate of inhibition of granuloma formation (%) | Increment of body weight (g) |
|---|---|---|---|---|
| Control Group | — | 287 | — | 62.0 |
| administered with Compound | | | | |
| No. 1 | 25 | 135 | 53 | 60.3 |
|  | 50 | 80 | 72 | 61.1 |
| No. 2 | 25 | 98 | 64 | 59.3 |
|  | 50 | 69 | 76 | 61.5 |
| No. 4 | 25 | 146 | 49 | 62.5 |
|  | 50 | 101 | 65 | 63.4 |
| Positive control group administered with | | | | |
| indomethacin | 3 | 175 | 39 | 55.3 |
| prednisolone | 3 | 158 | 45 | 41.0 |

The rate of inhibiting the granuloma formation was obtained from the following formula:

$$\text{Rate of inhibition} = \left(1 - \frac{T}{C}\right) \times 100$$

wherein T is the average weight of granuloma in the test group and C is the average weight of granuloma in the control group.

As is understood from Table 3, the present compounds inhibit the granuloma formation without reducing the body weight of the rat. As a result of carrying out the autopsy of the animal subjected to the antigranuloma test, in the group to which indomethacin or prednisolone has been administered, hemorrhage from the gastric mucosa and formation of stomach ulcer were found, and in the group to which prednisolone had been administered, atrophy of the thymus was significantly found. However, in the group to which the present compound had been administered, no abnormal findings were recognized as compared to the control groups.

(5) Inhibitory activity of adjuvant arthritis

The activity of the present compound in inhibiting the adjuvant arthritis was examined while using groups of 8 week old male Lewis rats and according to the administration and on the next day after finishing the administration.

The results of the test are shown in Table 4 as the increment of the volume of the hind paw and the rate of inhibiting the increase of the volume thereof.

The increment of the volume of the hind paw at the beginning of the administration, namely after 21 days of the injection of the complete adjuvant ($I_1$), and the increment of that after the finishing of the injection, namely after 36 days of the injection of the complete adjuvant ($I_2$) are respectively as follows.

$$I_1 = V_1 - V_0$$

and $$I_2 = V_2 - V_0$$

wherein $V_0$ is the volume of the hind paw just before the injection, $V_1$ is that after 21 days of the injection and $V_2$ is that after 36 days of the injection.

The rate of inhibiting the increase of the volume of the hind paw, namely the activity of treating the adjuvant arthritis is obtained by the following formula:

$$\text{Rate of inhibition (\%)} = \left(1 - \frac{I_2}{I_1}\right) \times 100$$

TABLE 4

| Group | Amount of administration (mg/kg/day) | Increment of the volume of hind paw after 21 days of injection (ml) | Increment of the volume of hind paw after 36 days of injection (ml) | Rate of inhibiting adjuvant arthritis (%) |
| --- | --- | --- | --- | --- |
| Control | — | 1.31 | 1.25 | — |
| Test group administered with the present compound | | | | |
| No. 1 | 25 | 1.29 | 0.65[1)] | 50 |
|  | 50 | 1.28 | 0.59[2)] | 54 |
| No. 2 | 25 | 1.32 | 0.51[2)] | 61 |
|  | 50 | 1.30 | 0.53[2)] | 59 |
| Positive control group administered with prednisolone | 3 | 1.27 | 0.71[1)] | 44 |

Notes:
[1)]significant with P less than 0.05
[2)]significant with P less than 0.01

As seen in Table 4, the present compound showed an excellent effect on treating adjuvant arthritis.

The present invention will be explained more in detail while referring to the following non-limiting Preparation Examples and Examples.

PREPARATION EXAMPLE 1

Preparation of a pharmaceutical composition

The following components were uniformly mixed thereby obtaining a pharmaceutical composition in a powder form and a minute particle form. The composition was filled in capsules to be capsular preparation.
10 parts by weight of Compound No. 1,
15 parts by weight of heavy magnesium oxide and
75 parts by weight of lactose.

PREPARATION EXAMPLE 2

Preparation of a pharmaceutical composition

The following components were uniformly mixed and kneaded, and then, the thus kneaded material was crushed and formulated into granules, the granules being dried and sifted thereby obtaining a granular pharmaceutical composition.
45 parts by weight of Compound No. 2,
10 parts by weight of starch,
20 parts by weight of lactose,
3 parts by weight of polyvinylalcohol and
22 parts by weight of water.

EXAMPLE 1

Synthesis of N-(n-octyl)-3,4-dihydroxybenzamide (Compound No. 1)

Into 76 ml of an aqueous 2N solution of potassium hydroxide, 7.81 g of 3,4-dihydroxybenzoic acid were dissolved, and while stirring the solution in an ice water bath, 13.0 ml of acetic anhydride were added dropwise to the cooled solution, and kept stirring for 30 min. The reaction mixture was acidified by adding concentrated hydrochloric acid, and the thus precipitated colorless crystals were collected by filtration, dissolved in ethyl acetate and the thus formed solution was dehydrated with anhydrous sodium sulfate.

By crystallization after condensing the thus dehydrated solution, 9.30 g of 3,4-diacetoxybenzoic acid (IV) showing a melting point of 155.0° to 156.0° C. were obtained.

After adding 19 g of thionyl chloride to 9.30 g of the compound (IV), the mixture was refluxed with stirring for 30 min and the excess thionyl chloride was distilled off from the reaction mixture under a reduced pressure to obtain 9.97 g of 3,4-diacetoxybenzoic acid chloride (V) as a colorless oily matter.

9.97 g of the thus obtained compound (V) were dissolved into 40 ml of dichloromethane, and this solution was added dropwise to the solution of 5.04 g of n-octylamine, 40 ml of dichloromethane and 4.5 g of triethylamine under cooling, and then kept stirring for one hour.

Thereafter, the solvent was distilled off from the reaction mixture under a reduced pressure and both 150 ml of ethyl acetate and 60 ml of an aqueous 1N hydrochloric acid solution were added to the distillation residue, and the mixture was shaken and left to stand for a while, and the thus separated organic layer was washed with water, dried and the solvent was distilled off from the organic layer, thereby obtaining 13.7 g of crude compound (VI), N-(n-octyl)-3,4-diacetoxybenzamide. By hydrolyzing the crude compound (VI) with the solution consisting of 5.09 g of potassium hydroxide, 50 ml of methanol and 2 ml of water and acidifying with hydrochloric acid, the crude crystals were precipitated and collected by filtration and then by recrystallization from benzene 7.47 g of N-(n-octyl)-3,4-dihydroxybenzamide (Compound No. 1) was obtained as colorless crystals (melting point: 118.0° to 120.0° C., yield: 73%). The elementary analytical data of the thus obtained Compound No. 1 are as follows.

|  | C (%) | H (%) | N (%) |
| --- | --- | --- | --- |
| Found | 68.20 | 8.80 | 5.30 |
| Calcd. as $C_{15}H_{22}NO_3$ | 67.90 | 8.74 | 5.28 |

Infrared absorption spectrum of Compound No. 1 is shown in FIG. 1.

EXAMPLES 2 to 7

Compounds Nos. 2 to 7 were synthesized in the same process as in Example 1, the major properties thereof being shown in Table 5. FIGS. 2 to 7 are infrared absorption spectra of the respective present compounds, Compounds Nos. 2 to 7.

TABLE 5

| Number of compound | Name of the present compound | Molecular formula | Melting point (°C.) | Elementary analytical data (%) | | | Yield |
|---|---|---|---|---|---|---|---|
| | | | | C | H | N | |
| 2 | N-(2-pyridyl)-3,4-dihydroxybenzamide | $C_{12}H_{10}N_2O_3$ | 220.0 to 221.0 | 62.40 (62.60) | 4.20 (4.30) | 12.00 (12.17) | 73 |
| 3 | N-(n-butyl)-3,4-dihydroxybenzamide | $C_{11}H_{15}NO_3$ | 139.5 to 140.5 | 63.00 (63.14) | 7.30 (7.23) | 6.70 (6.69) | 71 |
| 4 | 3,4-dihydroxybenzipiperidide | $C_{12}H_{15}NO_3$ | 185.5 to 187.0 | 65.10 (65.14) | 6.80 (6.83) | 6.20 (6.33) | 81 |
| 5 | N-(n-dodecyl)-3,4-dihydroxybenzamide | $C_{19}H_{31}NO_3$ | 115.0 to 116.0 | 70.90 (70.99) | 10.00 (9.72) | 4.40 (4.36) | 85 |
| 6 | N-(ω-phenylpropyl)-3,4-dihydroxybenzamide | $C_{16}H_{17}NO_3$ | 140.0 to 142.0 | 70.10 (70.83) | 6.30 (6.32) | 5.00 (5.16) | 67 |
| 7 | 3,4-dihydroxybenz-N-methylpiperazide | $C_{12}H_{16}N_2O_3$ | 219.0 to 220.0 | 60.9 (61.0) | 6.80 (6.83) | 11.60 (11.86) | 52 |

Note:
The parenthesized figures show the theoretical values calculated on the molecular formulae, respectively.

What is claimed is:

1. A method for treatment of inflammatory diseases, which comprises administering to patients suffering from inflammatory diseases an effective dosage amount of a compound of dihydroxybenzamide represented by the formula (I):

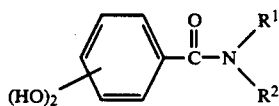

(I)

wherein $R^1$ represents a hydrogen atom or a lower alkyl group and $R^2$ represents a straight chain-alkyl group having 4 to 12 carbon atoms, a branched chain-alkyl group having 4 to 12 carbon atoms, a cyclo-alkyl group having 4 to 12 carbon atoms or a

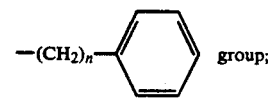 group;

wherein n is an integer of 1 to 6;
with the proviso that said compound is not represented by the formula:

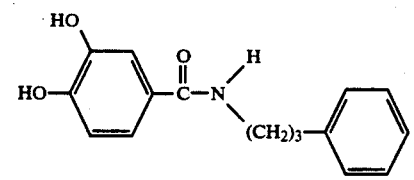

2. The method according to claim 1, wherein said compound of dihydroxybenzamide is N-(n-octyl)-3,4-dihydroxybenzamide.

3. The method according to claim 1, wherein said compound of dihydroxybenzamide is N-(n-butyl)-3,4-dihydroxybenzamide.

4. A method for the treatment of inflammatory diseases, which comprises administering to patients suffering from inflammatory diseases an effective amount of N-(n-dodecyl)-3,4-dihydroxybenzamide.

* * * * *